(12) United States Patent
Schultz

(10) Patent No.: US 8,128,895 B2
(45) Date of Patent: *Mar. 6, 2012

(54) INTEGRATED PRODUCTION OF FCC-PRODUCED C3 AND CUMENE

(75) Inventor: Michael A. Schultz, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/846,395

(22) Filed: Jul. 29, 2010

(65) Prior Publication Data

US 2010/0310432 A1    Dec. 9, 2010

Related U.S. Application Data

(62) Division of application No. 11/924,975, filed on Oct. 26, 2007, now Pat. No. 7,795,486.

(51) Int. Cl.
| | |
|---|---|
| B01J 8/00 | (2006.01) |
| B01J 19/00 | (2006.01) |
| B01J 8/02 | (2006.01) |
| B01J 8/18 | (2006.01) |
| F27B 15/00 | (2006.01) |
| F27B 15/08 | (2006.01) |
| F27B 15/14 | (2006.01) |
| F27B 15/16 | (2006.01) |
| C07C 2/64 | (2006.01) |
| C07C 15/067 | (2006.01) |
| C07C 2/56 | (2006.01) |
| C10G 45/00 | (2006.01) |
| C10G 45/58 | (2006.01) |

(52) U.S. Cl. ........ 422/608; 422/129; 422/139; 422/140; 422/141; 422/142; 422/143; 422/144; 422/145; 422/147; 422/600; 422/609; 422/620; 422/621; 422/211; 422/198; 585/448; 585/450; 585/709; 585/719; 208/216 R; 208/217; 208/264

(58) Field of Classification Search .................. 422/129, 422/139–147, 600, 608–609, 620–621, 211, 422/198; 585/448, 450, 709, 719, 910; 210/216 R, 210/217, 263–264; 208/216 R, 217, 263–264

See application file for complete search history.

(56) References Cited

U.S. PATENT DOCUMENTS

| | | | | | |
|---|---|---|---|---|---|
| 3,215,745 | A | * | 11/1965 | Frank | 568/572 |
| 4,249,030 | A | * | 2/1981 | Chapman et al. | 585/716 |
| 5,856,607 | A | * | 1/1999 | Kim | 585/448 |
| 6,576,805 | B2 | * | 6/2003 | Keady et al. | 585/802 |
| 7,914,754 | B2 | * | 3/2011 | Schultz | 422/620 |

* cited by examiner

*Primary Examiner* — Walter D Griffin
*Assistant Examiner* — Natasha Young
(74) *Attorney, Agent, or Firm* — Mark R Willis

(57) ABSTRACT

Processing schemes and arrangements are provided for obtaining propylene and propane via the catalytic cracking of a heavy hydrocarbon feedstock and converting the propylene into cumene without separating the propane from the propane/propylene feed stream. The disclosed processing schemes and arrangements advantageously eliminate any separation of propylene from propane produced by a FCC process prior to using the combined propane/propane stream as a feed for a cumene alkylation process. A bottoms stream from the cumene column of the cumene alkylation process can be used and an absorption solvent in the FCC process thereby eliminating the need for a transalkylation reactor and a DIPB/TIPB column.

5 Claims, 3 Drawing Sheets

US 8,128,895 B2

INTEGRATED PRODUCTION OF FCC-PRODUCED C3 AND CUMENE

CROSS-REFERENCE TO RELATED APPLICATION

This application is a Division of prior copending U.S. application Ser. No. 11/924,975 which was filed Oct. 26, 2007, the contents of which are incorporated herein by reference thereto.

TECHNICAL FIELD

This disclosure relates generally to hydrocarbon processing. More specifically, this disclosure relates to the initial processing of hydrocarbon-containing materials into an intermediate stream including propylene and propane produced by the cracking of a heavy hydrocarbon feedstock. This disclosure also relates to the subsequent use of said intermediate stream in the making of valuable aromatics, such as cumene.

BACKGROUND OF THE RELATED ART

Light olefins serve as feed materials for the production of numerous chemicals. Light olefins have traditionally been produced through the processes of steam or catalytic cracking of hydrocarbons such as derived from petroleum sources. Fluidized catalytic cracking (FCC) of heavy hydrocarbon streams is commonly carried out by contacting relatively high boiling hydrocarbons with a catalyst composed of finely divided or particulate solid material. The catalyst is transported in a fluid-like manner by transmitting a gas or vapor through the catalyst at sufficient velocity to produce a desired regime of fluid transport. Contact of the oil with the fluidized catalyst results in the cracking reaction.

FCC processing is more fully described in U.S. Pat. No. 5,360,533, U.S. Pat. No. 5,584,985, U.S. Pat. No. 5,858,206 and U.S. Pat. No. 6,843,906. Specific details of the various contact zones, regeneration zones, and stripping zones along with arrangements for conveying the catalyst between the various zones are well known to those skilled in the art.

The FCC reactor serves to crack gas oil or heavier feeds into a broad range of products. Cracked vapors from an FCC unit enter a separation zone, typically in the form of a main column, that provides a gas stream, a gasoline cut, light cycle oil (LCO), heavy cycle oil (HCO) and clarified oil (CO) components. The gas stream may include hydrogen, $C_1$ and $C_2$ hydrocarbons, and liquefied petroleum gas ("LPG"), i.e., $C_3$ and $C_4$ hydrocarbons.

There is an increasing need for light olefins such as propylene for the production of polypropylene, isopropyl benzene (cumene) and the like as opposed to heavier olefins. Research efforts have led to the development of an FCC process that produces or results in greater relative yields of light olefins, i.e., propylene. Such processing is more fully described in U.S. Pat. No. 6,538,169.

Cumene is an important intermediate compound for the production of phenol, acetone, alpha-methylstyrene and acetophenone. A conventional FCC process produces a combined propane/propylene stream. The propane/propylene stream is typically run through a splitter or distillation column to separate the propylene from the propane. The operation of such a splitter is energy intensive in addition to construction and maintenance costs.

In view of the increasing need and demand for light olefins such as propylene and the use thereof in useful aromatics such as cumene, there is a need and a demand for improved processing and arrangements for the separation and recovery of light olefins from such FCC process effluent and the efficient conversion of those olefins into useful aromatic intermediates.

SUMMARY OF THE INVENTION

An integrated process is disclosed for (i) catalytically cracking (FCC) a heavy hydrocarbon feedstock, (ii) obtaining a combined propane/propylene stream, and (iii) reacting the propylene of the combined propane/propylene stream with benzene to produce a cumene product stream. The integrated process comprises contacting a heavy hydrocarbon feedstock with a hydrocarbon cracking catalyst in a fluidized reactor zone to produce a hydrocarbon effluent stream that includes propane and propylene. The process then further comprises separating the combined propane/propylene stream from the hydrocarbon effluent stream, passing the combined propane/propylene stream to an alkylation reactor, and reacting at least some of the propylene of the combined propane/propylene stream with benzene in the alkylation reactor to produce cumene.

By linking the FCC process directly to the cumene alkylation process, substantial capital and energy costs savings are achieved. First, the need for a propane/propylene splitter column is eliminated as propane is inert to the cumene alkylation process and does not hinder the process in any appreciable way. Second, along with the energy savings achieved by eliminating the propane/propylene splitter, additional energy savings are achieved by linking the intercooler used to cool the alkylation reactor to one of the splitter columns of the FCC process.

Another integration option involves eliminating the transalkylation section and the diisopropyl benzene (DIPB) column from the cumene alkylation process, and sending the cumene column bottoms to primary absorber in the FCC process for use as solvent. The cumene bottoms stream is used to supplement the debutanized gasoline recycle, which is used as a primary absorber solvent. If all of the propylene generated in the FCC process is used in the cumene alkylation, the cumene column bottoms would reduce the required debutanized gasoline recycle by 15-20%. The DIPB and triisopropyl benzene (TIPB) would ultimately end up as a high octane component in the gasoline product.

Finally, because the TIPB may be slightly too heavy for the gasoline pool, another alternative is to send the cumene column bottoms to the FCC main column, where the heavier species in this stream would be removed in a heavier fraction such as the heavy naphtha draw. The lighter species in this stream will still act to reduce the required debutanized gasoline recycle, as they will exit in the unstabilized gasoline that is recovered from the main column overhead.

Thus, in accordance with this disclosure, the propane is preferably not stripped from the combined propane/propylene stream prior to the combined propane/propylene stream entering the alkylation reactor. The propane content of the combined propane/propylene stream may range up to about 30 wt %.

The hydrocarbon effluent generated in the FCC process passes through a separation zone to form a separator liquid stream and a separator vapor stream. $C_2-$ hydrocarbon materials are stripped from the separator liquid stream in a stripper column to form a $C_3+$ hydrocarbon process stream substantially free of $C_2-$ hydrocarbons. This stripper column may be advantageously heated with heat generated in the alkylation reactor. Thus, heat may be transferred from the intercooler used to cool the cumene alkylation reactor to the stripper column to lessen the cooling duty of the intercooler and therefore, reducing cooling water costs.

The bottoms from the $C_2$- stripper is then passed through a debutanizer which generates a bottoms debutanized gasoline product stream, part of which can be used as absorber solvent, and an overhead $C_3$-$C_4$ stream. The overhead $C_3$-$C_4$ stream is then passed through a caustic treatment zone to remove hydrogen sulfide, an extraction unit to catalytically oxidize mercaptans present to disulfides via a caustic wash, and a $C_3$/$C_4$ splitter to remove mixed $C_4$ products to provide a $C_3$ overhead stream, which becomes the propane/propylene stream used for cumene alkylation.

The propane/propylene stream may be passed through a dryer, a regenerative COS treater to remove COS, and an arsine and/or phosphine treater to effect removal of trace amounts of arsine and/or phosphine prior to sending the propane/propylene stream to the cumene alkylation unit.

An integrated system is disclosed for (i) catalytically cracking a hydrocarbon feedstock, (ii) obtaining selected hydrocarbon fractions including a combined propane/propylene stream and (iii) reacting the propylene of the combined propane/propylene stream with benzene to produce a cumene product stream. The integrated system includes a fluidized reactor zone wherein the hydrocarbon feedstock contacts a catalyst to produce a cracked effluent stream including propane and propylene. The system also includes a separation zone for separating the cracked effluent stream into at least one separator liquid stream and a separator vapor stream. The at least one separator liquid stream includes $C_3$+ hydrocarbons; the separator vapor stream includes $C_2$- hydrocarbons. The system also includes stripper to remove $C_2$- hydrocarbons from the $C_3$+ hydrocarbon stream, a debutanizer to remove $C_5$+ hydrocarbons from the $C_3$+ hydrocarbon stream, a $C_3$/$C_4$ splitter to produce a propane/propylene stream and various units upstream and downstream of the $C_3$/$C_4$ splitter to remove impurities other than propane and propylene. The combined propane/propylene stream is fed through a process line to an alkylation reactor for reacting at least some of the propylene in the combined propane/propylene stream with benzene to form cumene.

Intercoolers used to cool the alkylation reactor can be used to supply heat to a splitter column of the FCC process system. The bottoms stream from the cumene column can be used as an absorber solvent or can be added to the cracked effluent stream at the main column of the FCC process.

Other advantages will be apparent to those skilled in the art from the following detailed description taken in conjunction with the appended claims and drawings.

DETAILED DESCRIPTION OF THE PRESENTLY PREFERRED EMBODIMENTS

Figure 1:
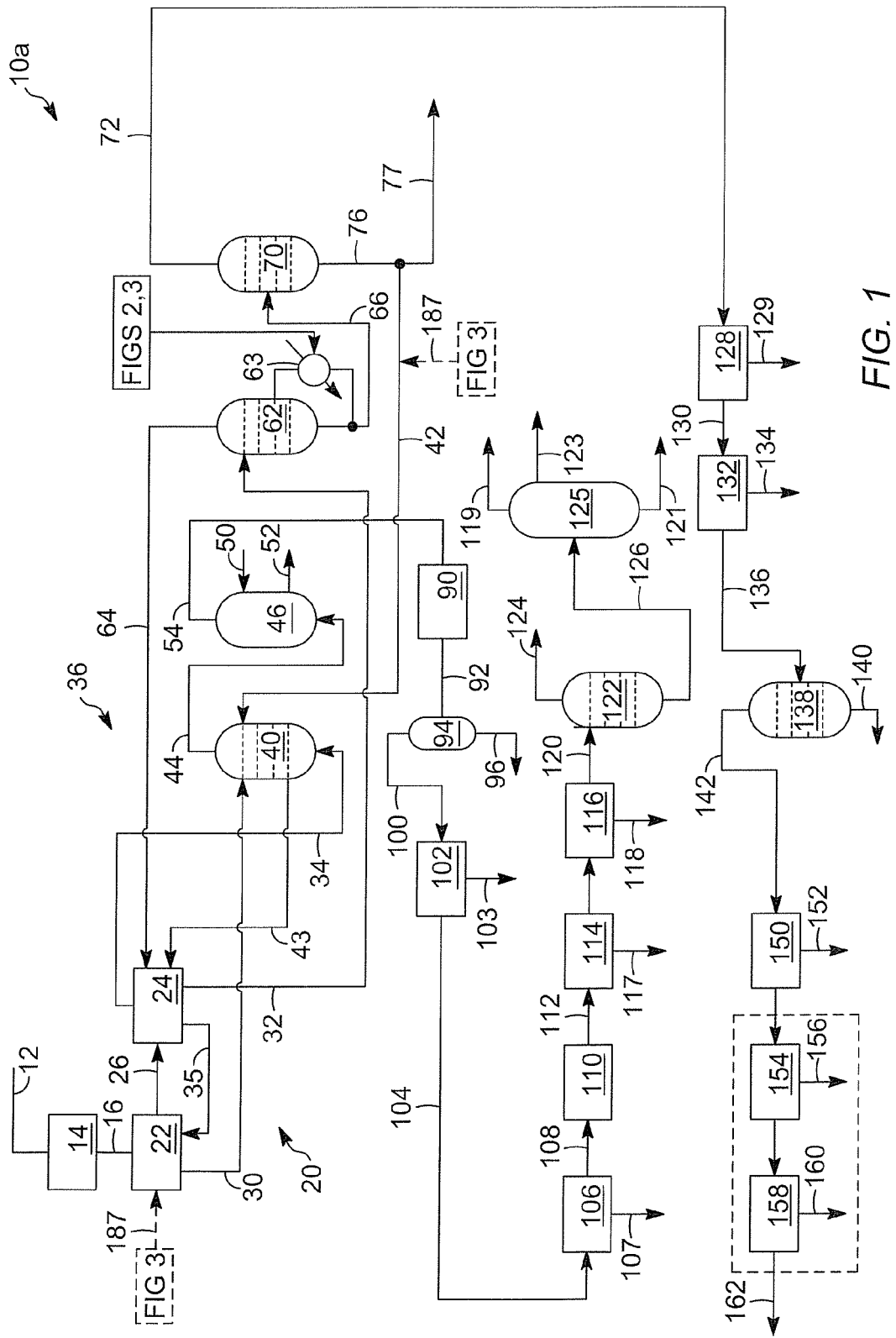
FIG. 1 is a simplified schematic diagram of a system for catalytic cracking a heavy hydrocarbon feedstock and obtaining selected hydrocarbon fractions, including light olefins via an absorption-based product recovery.
Figure 2:
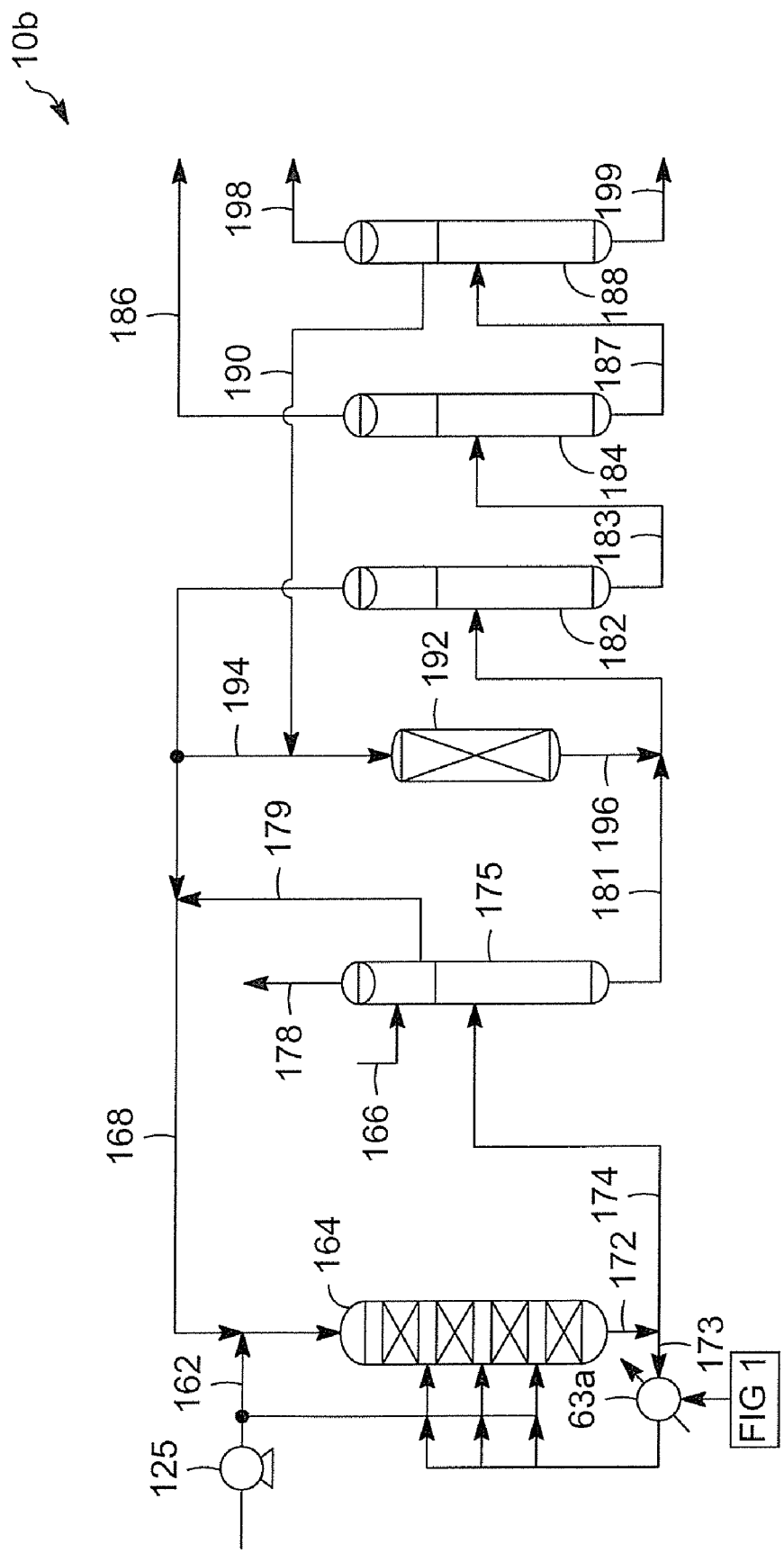
FIG. 2 is a simplified schematic diagram of a system for converting propylene to cumene that is integrated with the system of FIG. 1.
Figure 3:
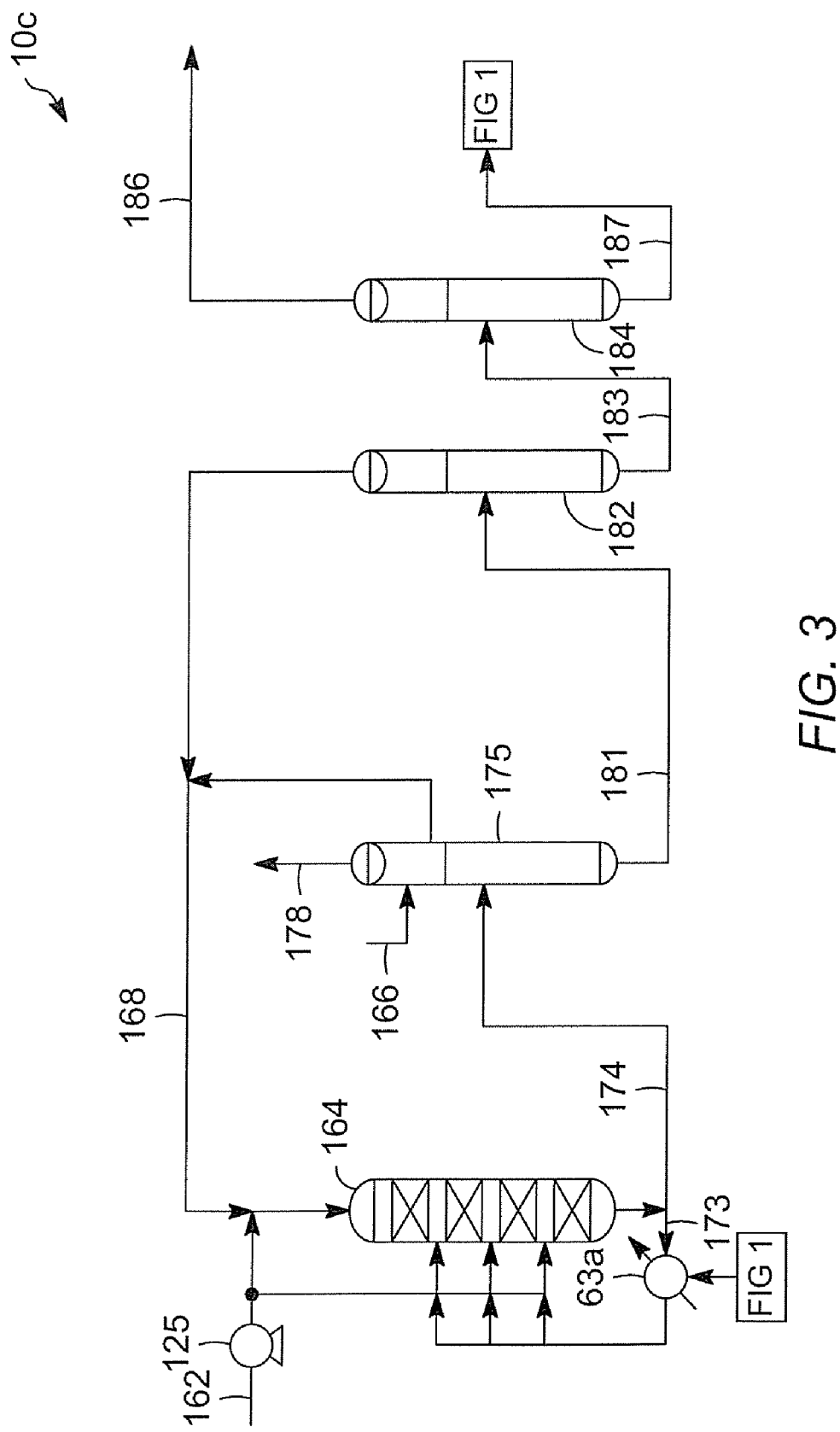
FIG. 3 is a simplified schematic diagram of another system for converting propylene to cumene that is also integrated with the system of FIG. 1.

FIG. 1 schematically illustrates a system 10a for catalytic cracking a heavy hydrocarbon feedstock and obtaining light olefins via absorption-based product recovery and FIGS. 2 and 3 schematically illustrates related systems 10b, 10c for efficiently converting the light olefins from the system 10a into one or more useful intermediates. Those skilled in the art and guided by the teachings herein provided will recognize and appreciate that the illustrated systems 10a, 10b, 10c have been simplified by eliminating some usual or customary pieces of process equipment including some heat exchangers, process control systems, pumps, fractionation systems, and the like. It may also be discerned that the process flows depicted in FIGS. 1-3 may be modified in many aspects without departing from the basic overall concepts disclosed herein.

In the cracking system 10a, a suitable heavy hydrocarbon feedstock stream is introduced via a line 12 into a fluidized reactor zone 14 wherein the heavy hydrocarbon feedstock contacts a hydrocarbon cracking catalyst zone to produce a hydrocarbon effluent comprising a range of hydrocarbon products, including light olefins such as propylene and light hydrocarbons such as propane.

Suitable fluidized catalytic cracking reactor zones for use in the practice of such an embodiment may, as is described in above-identified U.S. Pat. No. 6,538,169, include a separator vessel, a regenerator, a blending vessel, and a vertical riser that provides a pneumatic conveyance zone in which conversion takes place. The arrangement circulates catalyst and contacts the catalyst with the feed.

The FCC catalyst typically comprises two components that may or may not be on the same matrix. The two components are circulated throughout the reactor 14. The first component may include any of the well-known catalysts that are used in the art of fluidized catalytic cracking, such as an active amorphous clay-type catalyst and/or a high activity, crystalline molecular sieve. Molecular sieve catalysts are preferred over amorphous catalysts because of their much-improved selectivity to desired products. Zeolites are the most commonly used molecular sieves in FCC processes. Preferably, the first catalyst component comprises a large pore zeolite, such as a Y-type zeolite, an active alumina material, a binder material, comprising either silica or alumina and an inert filler such as kaolin.

The zeolitic molecular sieves appropriate for the first catalyst component should have a large average pore size. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. It has been found that Y zeolites with low rare earth content are preferred in the first catalyst component. Low rare earth content denotes less than or equal to about 1.0 wt % rare earth oxide on the zeolite portion of the catalyst. Octacat™ catalyst made by W. R. Grace & Co. is a suitable low rare earth Y-zeolite catalyst.

The second catalyst component comprises a catalyst containing, medium or smaller pore zeolite catalyst exemplified by ZSM-5, ZSM-11, ZSM-12, ZSM-23, ZSM-35, ZSM-38, ZSM-48, and other similar materials. U.S. Pat. No. 3,702,886 describes ZSM-5. Other suitable medium or smaller pore zeolites include ferrierite, erionite, and ST-5, developed by Petroleos de Venezuela, S. A. The second catalyst component preferably disperses the medium or smaller pore zeolite on a matrix comprising a binder material such as silica or alumina and an inert filer material such as kaolin. The second component may also comprise some other active material such as Beta zeolite. These catalyst compositions have a crystalline zeolite content of 10-25 wt % or more and a matrix material content of 75-90 wt %. Catalysts containing 25 wt % crystalline zeolite material are preferred. Catalysts with greater crystalline zeolite content may be used, provided they have satisfactory attrition resistance. Medium and smaller pore zeolites are characterized by having an effective pore opening diameter of less than or equal to 0.7 nm, rings of 10 or fewer members and a Pore Size Index of less than 31.

The total catalyst composition should contain 1-10 wt % of a medium to small pore zeolite with greater than or equal to 1.75 wt % being preferred. When the second catalyst component contains 25 wt % crystalline zeolite, the composition contains 4-40 wt % of the second catalyst component with a preferred content of greater than or equal to 7 wt %. ZSM-5 and ST-5 type zeolites are particularly preferred since their high coke resistivity will tend to preserve active cracking sites as the catalyst composition makes multiple passes through the riser, thereby maintaining overall activity. The first catalyst component will comprise the balance of the catalyst composition. The relative proportions of the first and second components in the catalyst composition will not substantially vary throughout the FCC unit 14.

The high concentration of the medium or smaller pore zeolite in the second component of the catalyst composition improves selectivity to light olefins by further cracking the lighter naphtha range molecules. But at the same time, the resulting smaller concentration of the first catalyst component still exhibits sufficient activity to maintain conversion of the heavier feed molecules to a reasonably high level.

The relatively heavier feeds suitable for processing in accordance herewith include conventional FCC feedstocks or higher boiling or residual feeds. A common conventional feedstock is vacuum gas oil which is typically a hydrocarbon material prepared by vacuum fractionation of atmospheric residue and which has a broad boiling range of from 315-622° C. (600-1150° F.) and, more typically, which has a narrower boiling point range of from 343-551° C. (650-1025° F.). Heavy or residual feeds, i.e., hydrocarbon fractions boiling above 499° C. (930° F.), are also suitable. The fluidized catalytic cracking processing the invention is typically best suited for feedstocks that are heavier than naptha range hydrocarbons boiling above about 177° C. (350° F.).

The effluent or at least a selected portion thereof is passed from the fluidized reactor zone 14 through a line 16 into a hydrocarbon separation system 20, which may include a main column section 22 and a staged compression section 24. The main column section 22 may desirably include a main column separator and associated main column receiver where the fluidized reactor zone effluent can be separated into desired fractions including a main column vapor stream that is passed through line 26 to the two stage compressor 24, and a main column liquid stream, which is passed through line 30 to the absorber 40. Other fraction lines such as including a heavy gasoline stream, a light cycle oil ("LCO") stream, a heavy cycle oil ("HCO") stream and a clarified oil ("CO") stream, for example, may not be shown or specifically described.

The main column vapor stream line 26 is introduced into the staged compression section 24. The staged compression section 24 results in the formation of a high pressure separator liquid stream in a line 32 and a high pressure separator vapor stream in a line 34. While the pressure of such high pressure liquid and high pressure vapor can vary, in practice such streams are typically at a pressure ranging from about 1375 kPag to about 2100 kPag (about 200 psig to about 300 psig). The compression section 24 may also result in the formation of a stream of spill back materials largely composed of heavier hydrocarbon materials and such as can be returned to the main column section 22 via the line 35.

The high pressure separator liquid stream 32 includes $C_3+$ hydrocarbons and is substantially free of carbon dioxide and hydrogen sulfide. The high pressure separator vapor stream 34 includes $C_2-$ hydrocarbons and typically includes some carbon dioxide and hydrogen sulfide.

The separator vapor stream line 34 is introduced into an absorption zone 36, which includes the primary absorber 40, where the separator vapor stream 34 is contacted with a debutanized gasoline material provided by the line 42 and the main column overhead liquid stream 30 to absorb $C_3+$ materials and separate $C_2$ and lower boiling fractions from the separator vapor stream. In general, the absorption zone 36 includes the primary absorber 40 that suitably includes a plurality of stages with at least one and preferably two or more intercoolers interspaced therebetween to assist in achieving desired absorption. In practice, such a primary absorber 40 includes about five absorber stages between each pair of intercoolers. The primary absorber 40 may include at least about 15 to 25 ideal stages with 2 to 4 intercoolers appropriately spaced between the stages.

$C_3+$ hydrocarbons absorbed in or by the debutanized gasoline stream 42 and main column liquid stream 30 in the absorber 40 can be passed via the line 43 back to the two-stage compressor 24 for further processing. The off gas from the primary absorber 40 passes via a line 44 to a secondary or sponge absorber 46. The secondary absorber 46 contacts the off gas with light cycle oil from a line 50. Light cycle oil absorbs most of the remaining $C_4$ and higher hydrocarbons and returns to the main fractionators via a line 52. A stream of $C_2-$ hydrocarbons is withdrawn as off gas from the secondary or sponge absorber 46 in the line 54 for further treatment as later described herein.

The high pressure liquid stream 32 from the compressor 24 is passed through to the stripper 62 which removes most of the $C_2$ and lighter gases through the line 64 and passes them back to the compressor 24. In practice, the stripper 62 can be operated at a pressure ranging from about 1375 kPag to about 2100 kPag (about 200 psig to about 300 psig) with a $C_2/C_3$ molar ratio in the stripper bottoms of less than 0.001 and preferably with a $C_2/C_3$ molar ratio in the stripper bottoms of less than about 0.0002 to about 0.0004.

As discussed in greater detail below, the reboiler heat exchanger 63 may be driven by heat generated in the alkylation reactor 164 shown in FIGS. 2-3. Specifically, one or more inter-coolers 63a (FIGS. 2-3) may be combined with the reboiler heat exchanger 63 (FIG. 1).

As shown, the $C_2$ and lighter gases in the line 64 are combined in the compressor 24 with the main column vapor stream 26 to form with high pressure separator vapor stream 34 that is fed into the primary absorber 40. The stripper 62 supplies a liquid $C_3+$ stream 66 to the debutanizer 70. A suitable debutanizer 70 includes a condenser (not shown) that desirably operates at a pressure ranging from about 965 kPag to about 1105 kPag (about 140 psig to about 160 psig), with no more than about 5 mol % $C_5$ hydrocarbons in the overhead and no more than about 5 mol % $C_4$ hydrocarbons in the bottoms. More preferably, the relative amount of $C_5$ hydrocarbons in the overhead is less than about 1-3 mol % and the relative amount of $C_4$ hydrocarbons in the bottoms is less than about 1-3 mol %.

A stream of $C_3$ and $C_4$ hydrocarbons from the debutanizer 70 is taken as overhead through line 72 for further treatment as described below and the bottoms stream 76 from the debutanizer 70 comprises gasoline, part of which forms the stream 42 which is fed to the top of the primary absorber 40 where it serves as the primary first absorption solvent. Another portion of the stream of debutanized gasoline is passed through the line 77 to a naphtha splitter (not shown), which may be a dividing wall separation column.

The $C_2-$ hydrocarbon stream 54 withdrawn from the secondary or sponge absorber 46 is passed through a further compression section 90 to form a compressed vapor stream 92 that is passed into a compression or discharge vessel 94. The discharge vessel 94 forms a liquid knockout stream generally composed of heavy components (e.g., $C_3+$ hydrocarbons that liquefy in the discharge vessel 94) and are withdrawn in the line 96. The discharge vessel 94 also forms an overhead vapor stream 100 primarily comprising $C_2-$ hydrocarbons, with typically no more than trace amounts (e.g., less than 1 wt %) of $C_3+$ hydrocarbons.

The overhead stream 100 is passed to an amine treatment section 102 to remove $CO_2$ and $H_2S$. The utilization of amine treatment system 102 for carbon dioxide and/or hydrogen sulfide removal is well known in the art. Conventional such amine treatment systems typically employ an amine solvent such as methyl diethanol amine (MDEA) to absorb or otherwise separate $CO_2$ and $H_2S$ from hydrocarbon stream materials. A stripper or regenerator is typically subsequently used to strip the absorbed $CO_2$ and $H_2S$ from the amine solvent, permitting the reuse of the amine solvent.

While such amine treatment has proven generally effective for removal of carbon dioxide from various hydrocarbon-containing streams, the application of such amine treatment to ethylene-rich hydrocarbon and carbon dioxide-containing streams, such as being processed at this point of the subject system, may experience some undesired complications as some of the olefin material may be co-absorbed with the $CO_2$ and $H_2S$ in or by the amine solvent. Such co-absorption of olefin material undesirably reduces the amounts of light olefins available for recovery from such processing. Moreover, during such subsequent stripper processing of the amine solvent, the presence of such olefin materials can lead to polymerization. Such polymerization can lead to degradation of the amine solvent and require expensive off-site reclamation processing.

It may be desirable to utilize an amine treatment system such as includes or incorporates a pre-stripper interposed between the amine system absorber and the amine system stripper/regenerator. Such an interposed pre-stripper, can desirably serve to separate hydrocarbon materials, including light olefins such as ethylene, from the carbon dioxide and amine solvent prior to subsequent processing through the regenerator/stripper. A $CO_2/H_2S$ outlet is shown at 103.

A stream 104 containing $C_2-$ hydrocarbons substantially free of carbon dioxide is passed to a dryer section 106 with a water outlet line 107. A stream containing dried $C_2-$ hydrocarbons substantially free of carbon dioxide is passed via a line 108 to an acetylene conversion section or unit 110. As is known in the art, acetylene conversion sections or units are effective to convert acetylene to form ethylene. Thus, an additionally ethylene-enriched process stream 112 is withdrawn from the acetylene conversion section or unit 110 and passed to the optional dryer 114 or to the $CO_2$, carbonyl sulfide ("COS"), arsine and/or phosphine treater 116 as is known in the art to effect removal of $CO_2$, COS, arsine and/or phosphine.

Water is withdrawn from the dryer 114 through the line 117. $CO_2$, COS, Arsine and/or Phosphine are withdrawn through the line 118, and the treated stream 120 is introduced into a demethanizer 122. A suitable demethanizer 122 may include a condenser (not specifically shown) that desirably operates at a temperature of no greater than about −90° C. (−130° F.), more preferably operates at a temperature in the range of about −90° C. to about −102° C., preferably about −96° C. (−130° to about −150° F., preferably at about −140° F.). In addition, the demethanizer 122 may operate with a methane to ethylene molar ratio in the bottoms of no greater than about 0.0005 and, more preferably at a methane to ethylene molar ratio in the bottoms of no greater than about 0.0003 to about 0.0002.

The overhead stream 124 of methane and hydrogen gas from the demethanizer 122 may be used as a fuel or, if desired, taken for further processing or treatment such as to a pressure swing absorption unit (not shown) for $H_2$ recovery. The demethanizer outlet stream 126 is passed to a $C_2/C_2$=splitter 125, which produces an ethylene stream 123, a ethane stream 121 and a light ends overhead stream 119.

Still referring to FIG. 1, the stream 72 containing $C_3$ and $C_4$ hydrocarbons taken overhead from the debutanizer 70 may contain some significant relative amounts of hydrogen sulfide and is therefore preferably passed to a sulfide removal treatment unit 128, such as an amine treatment section, where hydrogen sulfide is removed through the line 129 and the treated stream 130 is passed to an optional extraction unit 132 to catalytically oxidize mercaptans present to disulfides via a caustic wash, which are removed through the line 134.

The resulting stream 136 is passed to the $C_3/C_4$ splitter 138. A suitable $C_3/C_4$ splitter includes a condenser (not specifically shown) that desirably operates at a pressure in the range of about 1650 kPag to about 1800 kPag (about 240 psig to about 260 psig), preferably at a pressure of about 1724 kPa (about 250 psig) and desirably operates such that there is no more than about 5 mol % $C_4$s in the overhead product stream, preferably less than about 1 mol % $C_4$s in the overhead product stream and no more than about 5 mol % $C_3$s in the bottoms stream, preferably less than about 1 mol % $C_3$s in the bottoms stream.

The $C_3/C_4$ splitter 138 forms a bottoms stream 140 of $C_4+$ hydrocarbons for use as either for product recovery or further desired processing, as is known in the art. The $C_3/C_4$ splitter 138 also forms a stream 142 composed primarily of $C_3$ hydrocarbons.

The propylene/propane stream 142 may be passed to dryer 150 for the removal of water through the line 152 before being passed on to a regenerative COS treater 154 to remove COS through the line 156 before being passed through the arsine and/or phosphine treater 158 to effect removal of trace amounts of arsine and/or phosphine through the line 160 and producing a propane/propylene product stream 162.

Turning to FIG. 2, the combined propane/propylene stream 162 is introduced at various stages to the to the alkylation reactor 164, without pre-heating and without separating the propane, where the propylene reacts catalytically with benzene provided in the form of fresh benzene through the line 166 and recycled benzene through the line 168. Because propane is essentially inert to the cumene process system 10b, the need for an upstream propane/propylene splitter is not required. Further, pre-heating the cool propane/propylene stream 162 from the arsine/phosphine treater 122 is not required. As the material in the combined propane/propylene stream 162 is liquid, it may be delivered at pressures ranging from about 2900 to about 4000 kPa (~421 to ~580 psi) using a conventional pump 125.

Propylene in the stream 162 reacts with the benzene in the alkylation reactor 164 to produce a combined product stream 172 that will include cumene, DIPB, TIPB, propane, and unreacted ethylene and benzene. The combined alkylation product stream 172 is partially recycled back to the alkylation reactor 164 through the line 173 and also passed through the line 174 to the depropanizer column 175 where it is combined with the fresh benzene stream 166. Propane is taken as overhead through the line 178 and benzene is recycled through the line 179. The bottoms product 181, which includes some benzene as well as cumene, DIPB and TIPB, is passed to the benzene column 182 where benzene is taken as the overhead stream 168 and the cumene, DIPB, TIPB and heavies in the bottoms stream 183 is passed to the cumene column 184. Cumene is taken as the overhead stream and the DIPB, TIPB and heavies in the bottoms stream 187 is passed to the DIPB/TIPB column 188. A DIPB/TIPB rich overhead stream is routed to the tranalkylation reactor where it is combined with the benzene recycle stream 194 to produce a reactor effluent stream 196 with cumene, DIPB, TIBP and benzene that is combined with the bottoms stream 181 from the depropanizer 175 and passed to the benzene column 182. The DIPB/TIPB column 188 also produces an overhead drag stream 198 and a heavies bottoms stream 199.

The intercooler(s) 63a in the alkylation section 164 typically requires a cooling water utility. In accordance with this disclosure, integrating the alkylation intercooler(s) 63a (FIG. 2) with the $C_2$-stripper 62 (FIG. 1) reduces the need for additional heating by LP steam which would be required by the reboiler 63 (FIG. 1). All or most of the heat for the reboiler 63 can be provided by the intercooler 63a.

An additional integration option is illustrated in FIG. 3 and involves eliminating the transalkylation section 192 and the DIPB/TIBP column 188. The cumene column bottoms 187 is passed to the primary absorber 40 (FIG. 1) by combining the cumene bottoms stream 187 with the debutanized gasoline recycle stream 42 (FIG. 1) to supplement some of the debutanized gasoline recycle, reducing the amount of recycle that is required. If all of the propylene produced by the FCC process 10a is used in the cumene process 10c, the cumene column bottoms 187 would reduce the required debutanized gasoline recycle stream 42 by an amount ranging from about 15 to about 20%. The DIPB, TIBP and other heavies would ultimately end up as a high octane component in the gasoline product stream 77. Because the cumene column bottoms 187 contains a small fraction of heavy components (e.g., TIPB and heavies) that may be slightly too heavy for the gasoline product, another alternative shown in FIG. 3 is to send the cumene column bottoms 187 to the FCC main column 22, where the heavier species in this stream would be removed in a heavier fraction such as the heavy naphtha draw. The lighter species in this stream will still act to reduce the required debutanized gasoline recycle stream 42, as they will exit in the unstabilized gasoline stream 77 that is recovered from the main column overhead stream 26.

Thus, improved processing schemes and arrangements are provided for obtaining propylene and propane via the catalytic cracking of a heavy hydrocarbon feedstock and converting the propylene into cumene without separating the propane from the alkylation feed stream. More particularly, processing schemes and arrangements are provided that advantageously eliminate the need to separate propylene from propane produced by a FCC process prior to using the combined propylene/propane stream as a feed for cumene alkylation process.

The disclosed processes and schemes may be practiced in the absence of any element, part, step, component, or ingredient which is not specifically disclosed herein.

The invention claimed is:

1. An integrated system for catalytically cracking a hydrocarbon feedstock, obtaining selected hydrocarbon fractions including a combined propane/propylene stream and reacting the propylene of the combined propane/propylene stream with benzene to produce a cumene product stream, the integrated system comprising:
    a fluidized reactor zone wherein the hydrocarbon feedstock contacts a catalyst to produce an effluent stream including propane and propylene,
    a separation zone for separating the effluent stream into at least one separator liquid stream comprising propane and propylene and a separator vapor stream;
    at least one treatment zone to remove impurities from the separator liquid stream to provide a combined propane/propylene stream;
    a process line feeding the combined propane/propylene stream to an alkylation reactor of an alkylation zone for reacting at least some of the propylene in the combined propane/propylene stream with benzene to form cumene;
    a stripper for stripping $C_2-$ hydrocarbon materials from the separator liquid stream to form a $C_3+$ process stream substantially free of $C_2-$ hydrocarbons and that is treated in the at least one treatment zone to produce the combined propane/propylene stream; and
    at least one heat exchanger for transferring heat from the alkylation reactor to the stripper.

2. The integrated system of claim 1 further comprising an amine treatment zone for removing hydrogen sulfide from the combined propane/propylene stream.

3. The integrated system of claim 1 further comprising an extraction zone for catalytically oxidizing and removing mercaptans from the combined propane/propylene stream.

4. The integrated system of claim 1 further comprising a $C_3/C_4$ splitter to remove $C_4+$ hydrocarbons from the combined propane/propylene stream.

5. The integrated system of claim 1 further comprising one or more of a dryer, a COS treater, an arsine treater and a phosphine treater for removing contaminants from the combined propane/propylene stream upstream of the alkylation zone.

* * * * *